United States Patent [19]

Semrad

[11] Patent Number: 5,234,438
[45] Date of Patent: Aug. 10, 1993

[54] PROCESS AND DEVICE FOR CREATING NEW TUNNELS IN TISSUE

[76] Inventor: Neal Semrad, 2180 Cedarhurst Dr., Los Angeles, Calif. 90027

[21] Appl. No.: 925,806

[22] Filed: Aug. 3, 1992

Related U.S. Application Data

[63] Continuation-in-part of Ser. No. 686,048, Apr. 16, 1991, abandoned.

[51] Int. Cl.$^5$ ............................................. A61M 25/00
[52] U.S. Cl. ................................... 606/108; 604/264; 604/280; 604/272; 606/222
[58] Field of Search .................. 606/108, 222; 604/51, 604/52, 53, 264, 272, 280, 283

[56] References Cited

U.S. PATENT DOCUMENTS

| | | | |
|---|---|---|---|
| 3,656,486 | 4/1972 | Robertson | 606/108 |
| 3,805,794 | 4/1974 | Schlesinger | 604/283 |
| 4,345,601 | 8/1982 | Fukuda | 606/222 X |
| 4,490,136 | 12/1984 | Ekbladh et al. | 604/272 |
| 4,545,373 | 10/1985 | Christoudias | 606/108 |
| 4,585,437 | 4/1986 | Simms | 606/108 X |
| 4,680,029 | 7/1987 | Ranford et al. | 604/280 |
| 4,832,687 | 5/1989 | Smith, III | 604/51 |
| 4,834,723 | 5/1989 | Sheridan et al. | 604/280 X |
| 4,976,684 | 12/1990 | Broadnax, Jr. | 604/51 |

OTHER PUBLICATIONS

Journal of Clinical Oncology, vol. 5, No. 1 (Jan.), 1987; pp. 131–136. Marcus Troxell and Richard Mansour. A New Technique for Placement of Tunneled Subclavian Right Atrial Catheters: Experience with 130 Cases.

Annals of the Royal College of Surgeons of England (1985) vol. 67. K. C. Soo, et al. Long–term Venous Access Using a Subcutaneous Implantable Drug Delivery System.

Br. J. Anaesth. (1984), 56, 1369. P. Carl, et al. Fixation of Extradural Catheters by Means of Subcutaneous Tissue Tunnelling.

Urological Research (1983) 11:191–193. J. W. Hoekstra, et al. A New Method for Permanent Catheterisation in the Dog.

Br. J. Surg. 1985, vol. 72, Feb., 127, M. Mughal, et al. An Atraumatic Method of Tunnelling Cuffed Central Venous Catheters.

Surgery, Gynecology & Obstetrics, Apr. 1989, vol. 168, pp. 353–354. John H. Raff. An Atraumatic Tunnelling Device for Implantation of Right Atrial Catheters and Ports.

Surgery, Gynecology & Obstetrics, Nov. 1983, vol. 157 pp. 485–486. John H. Raff. An Easy Technique for Tunneling the Broviac Catheter.

Anesthesiology, 71:477–478, 1989. Allen H. Hord. A Method for Subcutaneous Tunneling of Epidural Catheters Using Readily Available Equipment.

Intensive Care Med. (1988) 15:46–48. B. Pigot, et al. Tunnelling of Two Central Venous Catheters Inserted Via a Single Venipuncture.

Surgery, Gynecology & Obstetrics, May 1987, vol. 164, pp. 476–478. A Technique for Replacement of Long Term Venous Access Catheters. Sylvia M. Ramos, et al.

*Primary Examiner*—Peter A. Aschenbrenner
*Attorney, Agent, or Firm*—Wagner & Middlebrook

[57] ABSTRACT

A process for tunneling in tissue to install catheters and the like includes insertion of a hollow needle through the skin and, exiting from the skin as limited by the length of the needle or the catheter to be installed. A suture is then fed through the needle after which pulling tip of diameter approximately the same as the catheter to be installed, is selected and the suture attached to the distal end of the pulling tip. The catheter is then fastened to the proximal end of the pulling tip and the free end of the suture pulled to pull the catheter through the tunnel defined by the suture. The needle and suture may be inserted successively a number of times if a longer catheter is to be installed and the pulling tip and catheter pulled through the tissue. A similar procedure may be implemented using a solid needle with a swaged-on suture.

12 Claims, 1 Drawing Sheet

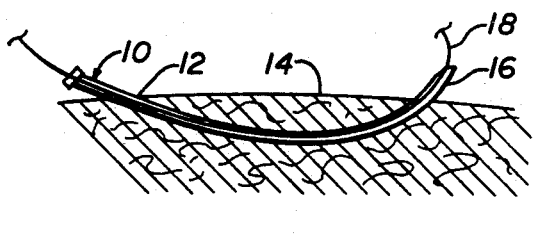
FIG. 1
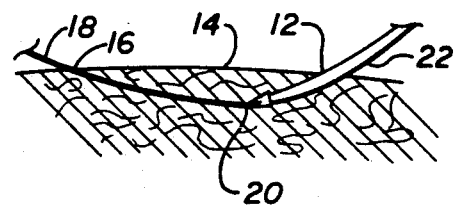
FIG. 2
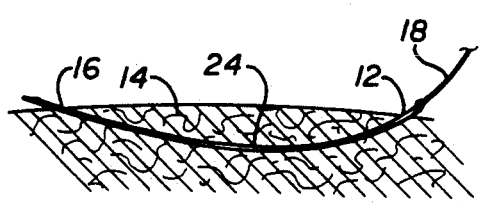
FIG. 3
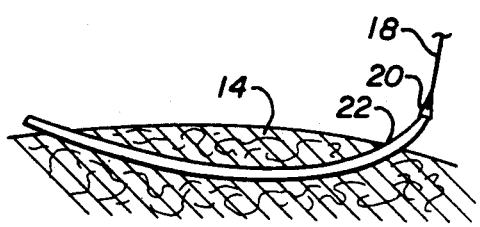
FIG. 5
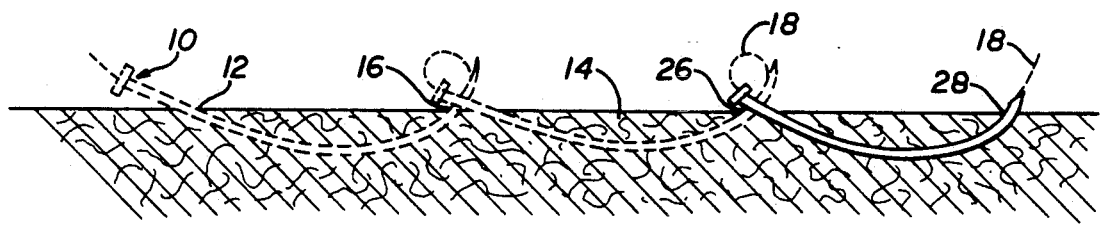
FIG. 4
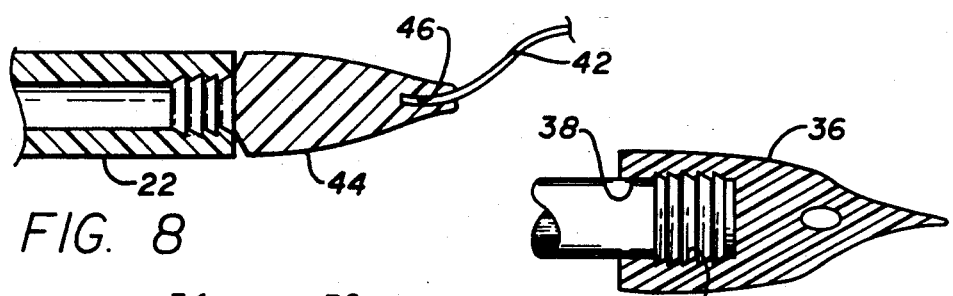
FIG. 8
FIG. 7
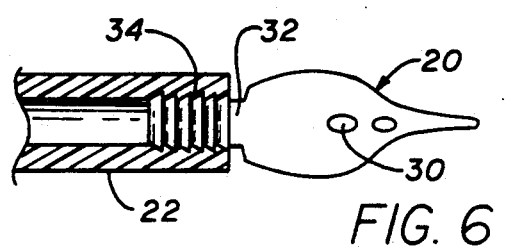
FIG. 6

PROCESS AND DEVICE FOR CREATING NEW TUNNELS IN TISSUE

This is a continuation-in-part of copending application Ser. No. 07/686,048 filed on Apr. 16, 1991, now abandoned.

BACKGROUND OF THE INVENTION

This invention relates to a process for tunneling through subcutaneous tissue to place catheters or similar sized devices in a patient as for chemotherapy, antibiotic administration, and similar uses and to a device for aiding in such process.

Tunneling of a variety of catheters for antibioses and/or patient comfort for permanent or semi-permanent catheters has been performed for decades. In the past this has been done by adapting various surgical instruments in order to create the tunnel. In general, techniques for developing new tunnels have involved the use of large trocar devices of varying sharpness that are most uncomfortable for the awake patient. Further, manipulating the large, cumbersome devices are technically difficult and increase risk for wound and catheter contamination.

A technique for replacement of Hickman catheters was reported by Romas and Lindens (Surgery, Gynecology & Obstetrics, Vol 164, May 1987) and works well for its particular purpose. It could not be used for closed-end catheters or any catheters in which the proximal length cannot be trimmed. It essentially uses a previously developed tunnel rather than creating a new one. References describing somewhat related techniques appear in the appendix at the end of the specification.

None of the techniques and devices described in the references known to applicant are as satisfactory for creating new tunnels for containing catheters, etc., as that described below.

BRIEF DESCRIPTION OF THE INVENTION

I have determined that an effective tunneling procedure involving a minimum of discomfort for the patient, minimum difficulty for the physician, minimum damage to tissue and minimum risk of infection can be implemented using my special pulling tips in connection with the procedure discussed below. The pulling tip itself is a small generally cylindrical member preferably formed of a suitable material such as polytetrafluorethylene (Teflon) or other plastic material having a tapered distal end with means such as an eye for securing a suture and an attaching structure at the proximal end for securely fastening itself to a catheter or other object which it is desired to install in the tissue. The pulling tip must be of material sufficiently rigid or hard to displace the tissue as it is pulled through.

Using a hollow needle, the area of catheter insertion and initial exit from the body is either entered by the needle or exited by the tip depending in which direction the tunneling is desired. Suture is then fed through the needle in the appropriate direction if one end has been attached to the pulling tip or in either direction if both ends of the suture are free. The needle is then removed. The procedure can be repeated as necessary for creating a longer tunnel for longer catheters. Alternatively, a needle with a swaged-on suture can be used instead of feeding the suture through a hollow needle. The appropriate pulling tip can then be attached to the suture (if it has not already been attached) the catheter attached to the proximal end of the pulling tip and by pulling on the free end of the suture, the catheter is caused to tunnel through the tissue through the path defined by the suture in the appropriate direction depending upon the catheter involved and the clinical situation. The small incisions for the catheter entry and exit sites are then closed as necessary.

BRIEF DESCRIPTION OF THE DRAWINGS

This invention may be more clearly understood from the following detailed description and by reference to the drawings in which:

FIG. 1 is a cross sectional view of a hollow needle inserted into tissue and a suture fed through the needle;

FIG. 2 is a cross sectional view of the suture and tissue of FIG. 1 with the needle removed and a pulling tip attached to the suture;

FIG. 3 is a cross sectional view of a large curved needle with a swaged-on suture being fed through the tissue;

FIG. 4 is a schematic diagram showing the technique for using successive insertions of the needle to provide for tunneling of longer catheters;

FIG. 5 is a cross sectional view showing the catheter in place prior to removing the pulling tip;

FIG. 6 is an elevational view, partly in section, of one form of my pulling tip; and FIG. 7 is an elevational view, partly in section, of another form of my pulling tip.

DETAILED DESCRIPTION OF THE INVENTION

Referring now to FIG. 1, a curved hollow needle 10 is shown inserted through the skin, at numeral 12, and into the tissue 14 of a patient, exiting through the skin at location 16. A suture 18 is shown fed through the needle 10. With the suture thus in place, the needle 10 is removed leaving the suture in the tunnel defined by the needle. The distal end of a pulling tip 20 may then be attached to one end of the suture 18. If only a short tunnel is required, a catheter 22 is then fastened to the proximal end of pulling tip 20 and the suture is then pulled through the tissue 14 via the tunnel established by the needle 10 and suture 18.

Rather than using a hollow needle 10, a large curved needle 24 with the suture 18 swaged-on may be used to implement the tunneling procedure as shown in FIG. 3.

Where longer catheters are to be employed, the tunneling may be implemented by using the "snake" technique illustrated in FIG. 4. As indicated in this view, the hollow needle 10 is inserted into the tissue at location 12 and the suture 18 is fed through the needle 10 as in FIG. 1, exiting at location 16. The needle is then removed and reinserted into the tissue 14 at location 16, exiting at location 26. The suture is then fed through the needle from location 16 to location 26. The needle 10 is then removed again and reinserted into the tissue at location 26, exiting at location 28. The suture is again fed through the needle, exiting at location 28, after which needle 10 is removed. This procedure may be repeated as desired until the suture in the tissue is of sufficient length to define essentially the tunnel location desired for the catheter. The distal end of the pulling tip 20 is then attached to the suture 18, the catheter 22 is attached to the proximal end of the pulling tip 20, and the unattached end of suture 18 is then pulled to carry the catheter through the tunnel defined by the position of the suture 18. The catheter 20 will tend to follow a fairly straight line subcutaneously from location 12 to location 28 rather than exactly following the somewhat up and down paths of needle 10.

The technique using the solid needle 24 with the swaged-on suture 18 is analogous to that described above. In this case, the needle 24 is inserted at location 12 and exits completely at location 16, pulling an adequate amount of suture 18 through the tunnel thus formed to complete the desired tunnel. The needle 24 is then reinserted at location 16, exiting completely at location 26, still carrying the extra length of suture required for subsequent insertion lengths. The needle 24 is again reinserted at location 26, exiting completely at location 28, and so on until the suture has been fed through the tissue for the length of the desired catheter installation. Following this, the pulling tip 20 is attached to suture 18, the catheter is attached to the proximal end of pulling tip 20, and the opposite end of the suture pulled to pull tip 20 and the catheter through tissue 14 as described. The pulling tip is pulled through and out of the tissue as shown in FIG. 5, at which time the pulling tip is disconnected from the catheter, and the opposite end of the catheter pulled to leave the distal end of the catheter in the tissue at the desired location. The opposite end of the catheter may then be trimmed and/or placed in the tissue as desired.

The size (diameter) of pulling tip employed will depend upon the size and type of catheter or other devices to be installed. The pulling tip 20 may be formed as shown in FIG. 6 with a taper toward the distal end and with an eye 30 formed in this end for attachment of the suture. The proximal end includes means to attach the catheter or other device. In FIG. 6 this is shown as including a smaller diameter section 32 including grooves 34 over which the catheter 22 is forced to secure the catheter from the inside. Because the path created by the needle and suture is much smaller than required for the catheter, the pulling tip must be of material which is sufficiently hard or firm to displace tissue as it is pulled. In addition to plastic materials such as polytetrafluorethylene (teflon) or polystyrene, the pulling tips may be of metals such as titanium or stainless steel.

FIG. 7 shows another type of pulling tip 36 in which the distal end includes an eye and in which the proximal end of pulling tip 36 includes internal attachment means for the catheter including a socket 38 having internal grooves 40 arranged to assist entry of the catheter but to resist pulling out. Such grooves may include shallow barbs, or such barbs may be formed in the internal surface of the pulling tip.

The above described embodiments of the present invention are merely descriptive of its principles and are not to be considered limiting. The scope of the present invention instead shall be determined from the scope of the following claims including their equivalents.

What is claimed is:

1. A process for tunneling in tissue to install catheters and the like comprising the steps of:
    a) inserting a needle through the skin and into the tissue for the length desired as limited by the length of said needle and exiting from the skin and causing a length of suture to follow the path of said needle through said tissue and exiting from the skin;
    b) selecting a pulling tip of diameter appropriate to the catheter to be installed and fastening said suture to the distal end of said pulling tip;
    c) fastening said catheter to the proximal end of said pulling tip; and
    d) pulling said suture to cause said pulling tip and said catheter to tunnel through the tissue as established by the path of said suture.

2. A process as claimed in claim 1 wherein following step a), said needle is reinserted at its previous exit point and caused to exit at a new location and said suture is again caused to follow the path of said needle through the tissue.

3. A process as claimed in claim 2 wherein said needle and suture are reinserted into the tissue as many times as required by the length of the catheter to be installed and said suture is pulled to pull the pulling tip and catheter through the tissue such that the desired length of catheter is tunneled through the tissue.

4. A process as claimed in claim 1 wherein said suture is swaged to said needle and follows said needle through said tissue.

5. A process for tunneling in tissue to install catheters and the like comprising the steps of:
    a) inserting a hollow needle through the skin and into the tissue for the length desired a limited by needle length and exiting from the skin;
    b) feeding a length of suture through the needle such that it extends out of the tissue on both ends;
    c) removing said needle;
    d) selecting a pulling tip appropriate to the catheter to be installed and fastening said suture the distal end of said pulling tip;
    e) fastening said catheter to the proximal end of said pulling tip; and
    f) pulling said suture to cause said pulling tip and said catheter to tunnel through the tissue as established by the path of said suture.

6. A process as claimed in claim 5 wherein following step c),:
    said needle is reinserted at its previous exit point and caused to exit at a new location and the suture reinserted through the needle such that the needle and suture exit the tissue at said new location; and said needle is removed.

7. A process as claimed in claim 6 wherein said needle is reinserted into the tissue and the suture fed through the needle and the needle removed as many times as required by the length of the catheter to be inserted and said suture is pulled to pull the pulling tip and catheter through the tissue such that the desired length of catheter is tunneled through the tissue.

8. For use in creating tunnels in a patient's tissue for installation of catheters or other similar sized devices wherein a suture has been fed through the tissue by any suitable means;
    a pulling tip of generally cylindrical cross section and of diameter approximating that of the catheter or other device to be installed in the tissue, said pulling tip being sharply tapered toward the distal end and of sufficient stiffness to penetrate and tunnel through the tissue, and including means to which said suture is attached, the proximal end of said pulling tip including fastening means for attaching said catheter thereto, whereby said pulling tip and said catheter or similar device may be pulled through and installed in a tunnel in said tissue.

9. A pulling tip as claimed in claim 8 wherein said means for attaching said suture includes an eye or port in the distal end of said pulling tip.

10. A pulling tip as claimed in claim 8 wherein said suture is swaged to the distal end of said pulling tip.

11. A pulling tip as claimed in claim 8 wherein said pulling tip includes a socket at its proximal end and said catheter is fastened in said socket.

12. A pulling tip as claimed in claim 8 wherein said fastening means includes means formed on the exterior of the proximal end of said pulling tip for securing said catheter to said pulling tip.

* * * * *